United States Patent [19]

van Hinsberg et al.

[11] Patent Number: 5,334,768

[45] Date of Patent: Aug. 2, 1994

[54] PROCESS FOR THE PRODUCTION OF A CYCLOALKANONE AND/OR A CYCLOALKANOL

[75] Inventors: Johannes G. van Hinsberg, Meerssen; Cornelis G. M. van de Moesdijk, Beek; Ivo Spaargaren, Geleen; Otto E. Sielcken, Sittard, all of Netherlands

[73] Assignee: DSM N.V., Heerlen, Netherlands

[21] Appl. No.: 12,859

[22] Filed: Feb. 3, 1993

[30] Foreign Application Priority Data

Mar. 2, 1992 [NL] Netherlands .......................... 9200187

[51] Int. Cl.$^5$ .............................................. C07C 45/58
[52] U.S. Cl. .................................... 568/341; 568/342; 568/835; 549/529
[58] Field of Search .................. 568/342, 835, 341; 549/529

[56] References Cited

U.S. PATENT DOCUMENTS 4,814,511 3/1989 Neubauer et al. .................. 568/342

FOREIGN PATENT DOCUMENTS 0192298 8/1986 European Pat. Off. ............ 568/341

1337300 11/1973 United Kingdom ................ 568/342

OTHER PUBLICATIONS

Chemical Abstracts 94: 15288q (1981).

*Primary Examiner*—James H. Reamer
*Attorney, Agent, or Firm*—Cushman, Darby & Cushman

[57] ABSTRACT

The invention relates to a process for the preparation of cycloalkanone and optionally cycloalkanol by causing a mixture containing cycloalkylhydroperoxide to react with cycloalkene under the influence of a catalyst, characterised in that the reaction is carried out with a short measure of cycloalkene relative to the cycloalkylhydroperoxide, under such conditions that virtually all of the cycloalkene reacts to cycloalkene oxide and optionally cycloalkanol and/or cycloalkanone, after which the mixture, optionally after decomposition of cycloalkylhydroperoxide and distillation of cycloalkane, is subjected to a first separation, in which cycloalkene oxide—and optionally other components—is separated, after which the cycloalkene oxide in the separated mixture is isomerised to substantially cycloalkanone, after which the cycloalkanone obtained—and optionally cycloalkanol—is recovered.

12 Claims, 2 Drawing Sheets

PROCESS FOR THE PRODUCTION OF A CYCLOALKANONE AND/OR A CYCLOALKANOL

The invention relates to a process for the production of cycloalkanone and optionally cycloalkanol by causing a mixture containing cycloalkylhydroperoxide to react with a cycloalkene under the influence of a catalyst.

Such a process is described for cyclohexane and cyclohexene in EP-A-268826. According to the process described therein virtually all the cyclohexylhydroperoxide, which is formed by oxidation of cyclohexane, reacts with a portion of the cyclohexene to form cyclohexene oxide or cyclohexane epoxide. Because of this, unreacted cyclohexene remains in the reaction mixture, which is hydrogenated to cyclohexane in a later step. The epoxide is also hydrogenated to cyclohexanol. A drawback of this process is that the cyclohexene is not optimally used and moreover—if cyclohexanone in particular is the desired end product—all the cyclohexanol must be dehydrogenated to cyclohexanone.

The invention provides a process for the production of cycloalkanone and optionally cycloalkanol that does not present the above drawback.

This aim is achieved because the invention provides a process for the production of cycloalkanone and optionally cycloalkanol by causing a mixture containing cycloalkylhydroperoxide to react with a cycloalkene, under the influence of a catalyst, which reaction is carried out with a short measure of cycloalkene relative to the cycloalkylhyroperoxide, under such conditions that virtually all the cycloalkene reacts to cycloalkene oxide and optionally cycloalkanol and/or cycloalkanone, after which, optionally after decomposition of cycloalkylhydroperoxide and distillation of cycloalkane, the mixture is subjected to a first distillative separation, in which cycloalkene oxide—and optionally other components—is separated, after which the cycloalkene oxide in the separated mixture is isomerised to substantially cycloalkanone, after which the cycloalkanone obtained—and optionally cycloalkanol—is recovered.

Optionally, the mixture obtained after isomerisation may, optionally after purification, be added to the bottom stream of the first distillative separation or may be used in another step in the recovery of cycloalkanone and/or cycloalkanol.

The advantages of the invention are exploited even more if the process according to the invention is used for the production of cycloalkanone, in which cycloalkanone is recovered in a further distillation step, after which cycloalkanol is separated from the residue and is converted into cycloalkanone, which is recirculated and is recovered in the aforementioned distillation step.

With the process according to the invention full advantage is taken of the saturation state of cycloalkene and hence hydrogenation steps and/or dehydrogenation steps as described in EP-A-268826, which are in principle unnecessary, are avoided.

Preferably, the cycloalkylhydroperoxide has 5–12 carbon atoms, more in particular 6, 8 or 12. The cycloalkene preferably has 5–12 carbon atoms, more in particular 6, 8 or 12. The process can be carried out in a preferred embodiment, according to which the cycloalkylhydroperoxide and the cycloalkene have the same number of carbon atoms. According to another preferred embodiment cyclohexylhydroperoxide is chosen as cycloalkylhydroperoxide and cyclooctene or cyclododecene is chosen as cycloalkene. For the sake of simplicity, in the following text of this patent the invention will be described more in particular on the basis of cyclohexane/cyclohexene because that appears to present an additional advantage, namely that the process according to the invention links up with cyclohexane oxidation processes used in existing plants.

Cyclohexylhydroperoxide is preferably produced in a known manner through oxidation of cyclohexane. The peroxide can be produced in a favourable manner in (preferably a series of) reactors, to which air is supplied at a temperature of between 140° and 250° C. and a pressure of between 0.4 and 2 MPa (4–20 bar), preferably in the absence of a metal catalyst. The resulting product is often a mixture containing 1–8 wt. %, preferably 2–6 wt. %, cyclohexylhydroperoxide and some cyclohexanone, cyclohexanol and byproducts.

The cyclohexene can be produced in a favourable way in a manner known per se through the partial hydrogenation of benzene. It is not necessary to use pure cyclohexene; solutions of 10–60 wt. % in an organic medium (preferably cyclohexane) are very suitable.

To ensure that the epoxidation takes place at a sufficiently high rate and to prevent the necessity of using undesirably large reactor volumes it is preferable to use 5–90% cycloalkylhydroperoxide mixtures. To this end cycloalkane can easily be evaporated from the hydroperoxide, optionally after washing with for example water. Optionally, an alcohol such as cyclohexanol may be added to for example cyclohexylhydroperoxide so that virtually all the cyclohexane can be removed via distillation. Preferably, the cycloalkylhydroperoxide used is a 10–80 wt. %, and more in particular a 15–70 wt. %, solution in an organic solvent.

The epoxidation reaction between the cyclohexylhydroperoxide and cyclohexene takes place under the influence of a catalyst at a temperature between 0° and 150° C., preferably between 20° and 120° C. The pressure is not critical; atmospheric pressure is advantageous because it involves a simple setup. Higher pressures are also possible, for example pressures of up to 2 MPa (20 bar), As catalyst use is made of a homogeneous or heterogeneous metal-containing compound with sufficient activity for the epoxidation reaction. Very suitable metals are molybdenum, tungsten, titanium and vanadium. Molybdenum complexes are preferable because of their high activity. The catalysts are used in amounts of between 0.001 and 5 wt. % relative to the reaction mixture.

The epoxidation reaction is carried out using an excess amount of cycloalkylhydroperoxide. The excess is usually more than 5 mol. % relative to the cycloalkene. In principle the upper limit is not critical, but the excess peroxide has to be recirculated or decomposed to cycloalkanol or cycloalkanone. It is hence preferable to use an excess amount of less than 100 mol. %. Excess amounts of between 10 and 50 mol. % are particularly preferable because they enable optimum reaction times and optimum efficient use of the peroxide.

The epoxidation reaction is preferably continued until virtually all of the cycloalkene is converted. As a rule, less than 3 wt. % cycloalkene will remain unreacted, preferably less than 2%, in particular less than 1%.

After the epoxidation reaction the reaction mixture is optionally first subjected to a cycloalkylhydroperoxide decomposition step. As a rule, processes for the preparation of cyclohexanone from cyclohexane already include such a decomposition step; it can be carried out with the aid of heterogeneous or homogeneous metal-containing catalysts (see e.g. DE-A-3222144, U.S. Pat. No. 4,503,257, U.S. Pat. No. 4,482,746, EP-A-270468 and EP-A-367326).

After this optional decomposition step the mixture is optionally subjected to washing with water, a bicarbonate solution or a sodium hydroxide solution, as is common in known processes for the preparation of cyclohexanone from cyclohexane. It has been found that if the reaction mixture is not exposed to water or a bicarbonate solution for longer than necessary virtually all of the cyclohexene oxide remains in the organic phase and a negligible amount decomposes or reacts.

After that, cycloalkane may optionally be removed through—preferably—distillative separation and other purification steps may optionally be carried out.

A next essential step is the isomerisation of cycloalkene oxide to substantially cycloalkanone. To this end cycloalkene oxide is first separated from the reaction mixture; this cycloalkene oxide may optionally contain 5-50 wt. % cycloalkane and/or other components. The separation is preferably effected through distillation, in which the cycloalkene oxide and other so-called light components are separated from cycloalkanol and cycloalkanone and heavier components. The isomerisation is preferably effected in the gas phase. Very suitable is for example the process described in EP-A-192298. The isomerisation preferably takes place under the influence of a precious metal catalyst (Pd or Pt in particular Pd) in the presence of hydrogen. Basic γ-alumina is preferably used as a carrier for the precious metal, the amount of precious metal being 0.5-5 wt. % relative to the carrier. The temperature is preferably between 140° and 250° C., more in particular between 175° and 225° C. The pressure is not critical; the partial hydrogen pressure is preferably between 1 and 1000 kPa.

Other processes for the isomerisation of cycloalkene oxide to cycloalkanone may however also be used.

The entire mixture obtained may be fed to the bottom stream from which the cycloalkene oxide has been removed (the main process stream), from which cycloalkanone is then recovered.

It is also possible to purify the isomerisation mixture first, separating for example only the components that are lighter than cycloalkanol and cycloalkanone, and then feed the remaining mixture to the process at a suitable point in the process. It is also possible to recover cycloalkanone directly from the isomerisation mixture.

It is preferable to return the isomerisation mixture to the main process stream, optionally after partial purification, and to recover cycloalkanone from said main process stream in the known manner and then dehydrogenate cycloalkanol to cycloalkanone and return the cycloalkanone-containing mixture thus obtained to the process at a suitable point in the process.

The process will be further elucidated with reference to two figures and examples, without being limited thereto.

Figure 1:
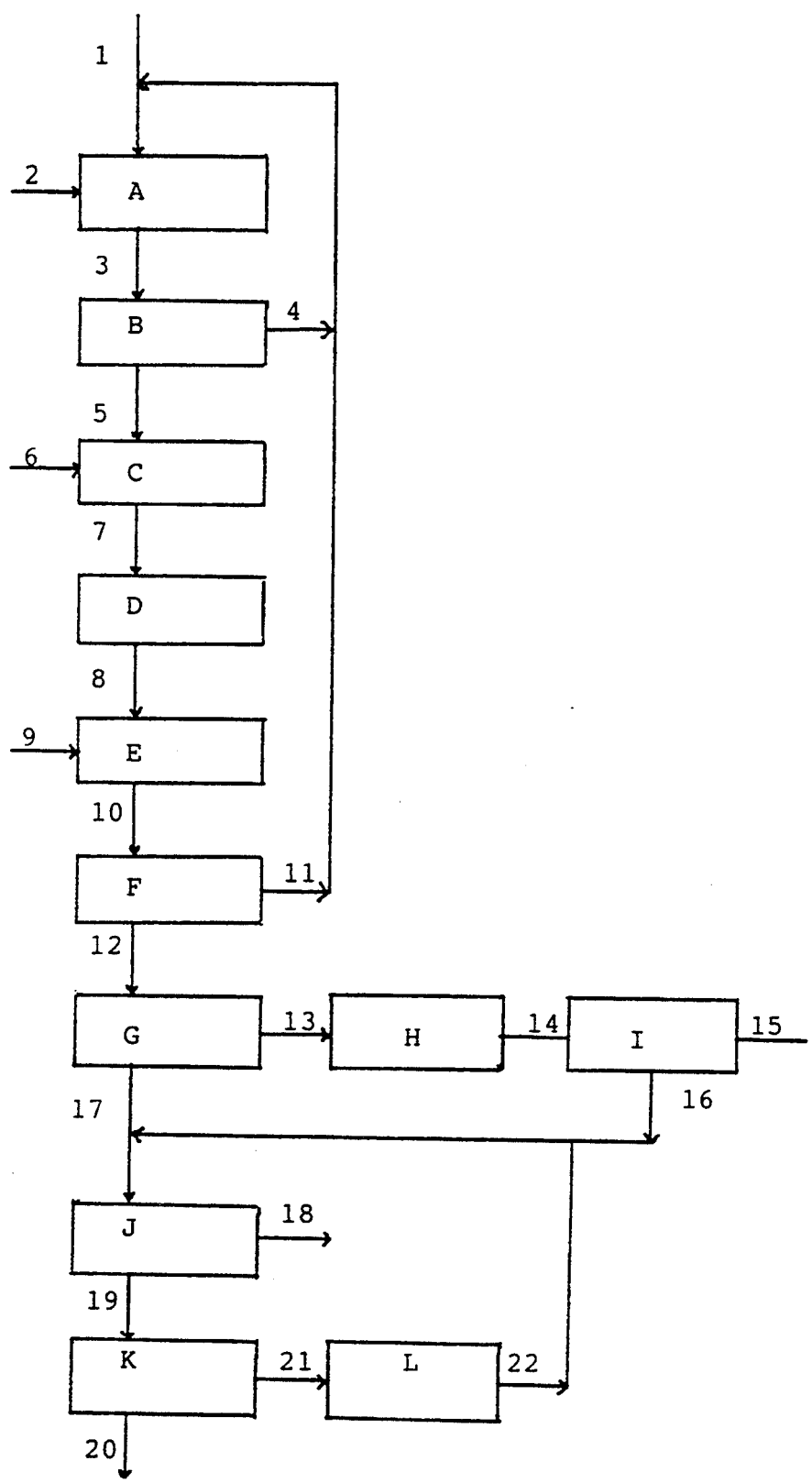
FIG. 1 shows a diagram of a preferred embodiment of the process.

In FIG. 1 (1) is a cyclohexane stream that is oxidized with air (2) in reactors (A). The resulting oxidized cyclohexane contains 1-8 wt. % cyclohexylhydroperoxide. In (B) this stream is partially stripped of cyclohexane (4), which is recirculated to (1). The resultant mixture (5) preferably contains 10-40 wt. % cyclohexylhydroperoxide. The epoxidation takes place in (C); stream (6) contains cyclohexene. The resultant reaction mixture (7) containing cyclohexene oxide and excess cyclohexylhydroperoxide is subjected to a cyclohexylhydroperoxide decomposition step in (D) for example by passing it over a heterogeneous decomposition catalyst. Then the reaction mixture (8) is washed with bicarbonate or water (9) in (E) and is thus stripped of acid by-products. In (F) cyclohexane is distilled from the process stream. The cyclohexane (11) is returned to (1). A process stream containing cyclohexene oxide (13) is separated from the process stream containing cyclohexanol and cyclohexanone (17) by means of distillation. Cyclohexene oxide is isomerised in (H) to obtain predominantly cyclohexanone. Light components are separated from this cyclohexanone-containing mixture (14) in (I). The light components may be burned to generate energy. The cyclohexanone-containing process stream (16) is fed to the bottom stream (17) of the cyclohexene oxidation distillation step (G) and cyclohexanone (18) is separated from that stream. This cyclohexanone may optionally be subjected to an additional purification step. Cyclohexanol (21) is separated from the heavy components (20) in the bottom stream (19) of the cyclohexanone distillation step (J). The heavy components can be burned or worked up. The cyclohexanol (21) is dehydrogenated in (L). Normally, the dehydrogenation is not complete and the resultant mixture (22) of cyclohexanone and cyclohexanol is returned to process stream (17) or process stream (12) (not indicated).

Figure 2:
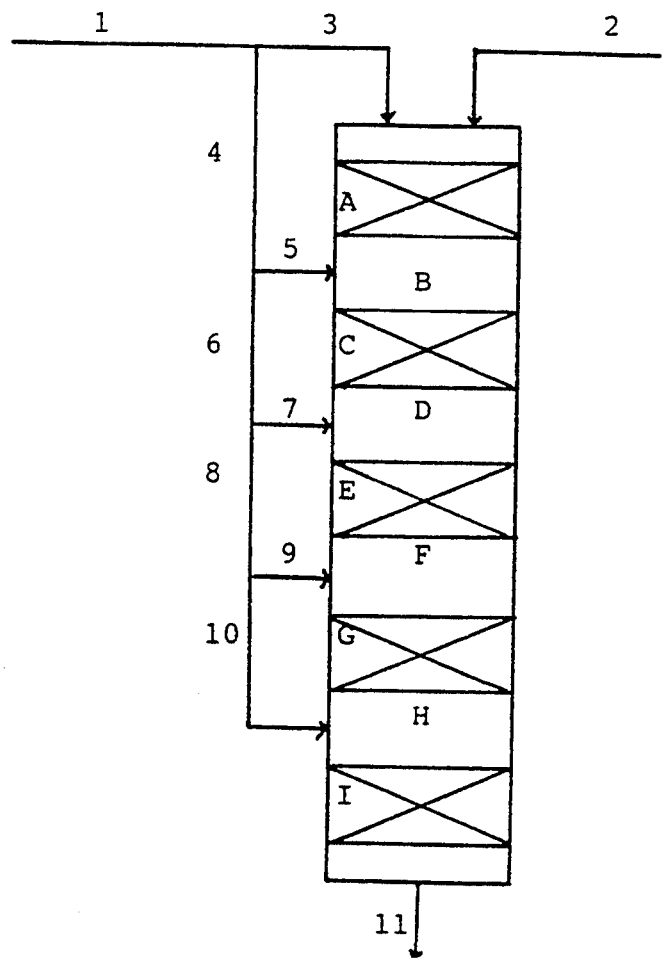
FIG. 2 is an example of an epoxidation reactor.

FIG. 2 shows an example of a multistage fixed-bed reactor, in which bed sections (A), (C), (E), (G) and (I) contain the epoxidation catalyst on a carrier. (B), (D), (F) and (H) are sections where the process streams are mixed, for example in a static mixer. The cyclohexylhydroperoxide-containing process stream (1) is split up into several streams (3-10); all of the cyclohexene (2) is fed directly to the reactor. By now using excess cyclohexene in the first 4 bed sections and using an excess of cyclohexylhydroperoxide in the last bed section only, cyclohexene is virtually completely converted into cyclohexene oxide in a relatively short time.

A possible distribution of the streams in FIG. 2, in the case of for example a 25% excess of cyclohexylhydroperoxide, is:

| stream | |
|---|---|
| 1: | 100 parts of cyclohexylhydroperoxide |
| 2: | 80 parts of cyclohexene |
| 3: | 40 parts of cyclohexylhydroperoxide |
| 4: | 60 parts of cyclohexylhydroperoxide |
| 5: | 20 parts of cyclohexylhydroperoxide |
| 6: | 40 parts of cyclohexylhydroperoxide |
| 7: | 10 parts of cyclohexylhydroperoxide |
| 8: | 30 parts of cyclohexylhydroperoxide |
| 9: | 5 parts of cyclohexylhydroperoxide |
| 10: | 25 parts of cyclohexylhydroperoxide |

In this way cyclohexene reacts in a 2:1 excess in the first 4 reactor sections and in the last reactor section cyclohexylhydroperoxide is present in a 5-fold excess relative to the cyclohexene still present there. The resulting reaction mixture (11) then still contains 20 parts of cyclohexylhydroperoxide in addition to cyclohexanol, cyclohexanone and cyclohexene oxide.

Such a concept is also very suitable if the epoxidation takes place under the influence of a homogeneous catalyst; in that case use can preferably be made of a series of stirred reactors.

EXAMPLE I

A reaction mixture consisting of 1 mol. % molybdenum on a carrier, 15.2 mmol cyclohexene, 18.7 mmol cyclohexylhydroperoxide, 9.7 mmol cyclohexanol, 3.8 mmol cyclohexanone and 28.8 mmol cyclohexane was heated to 80° C. for 3 hours. After this period the reaction mixture contained virtually no cyclohexene (0.12 mmol ), 1.51 mmol cyclohexylhydroperoxide, 14.78 mmol cyclohexene oxide, 5.45 mmol cyclohexanone, 25.26 mmol cyclohexanol and 28.8 mmol cyclohexane. For this reaction use was made of a solution of cyclohexylhydroperoxide concentrated to 40% that was obtained through uncatalysed air oxidation of cyclohexane and a 60% solution of cyclohexene in cyclohexane.

The resultant reaction mixture was maintained at 70° C. for half an hour after the addition of cobalt acetate to allow the remaining cyclohexylhydroperoxide to decompose to cyclohexanol and cyclohexanone.

The resulting reaction mixture was washed for 30 seconds using 1:1 Vol./Vol. 0.95M $NaHCO_3$ in water. GC analysis showed that only about 0.5% epoxide had disappeared from the organic layer. Acid byproducts and byproducts that readily dissolve in water were removed in this washing.

Then cyclohexane was distilled off; the resultant reaction mixture contained 10 wt. % cyclohexanone, 54 wt. % cyclohexanol and 36 wt. % cyclohexene oxide. Cyclohexene oxide was distilled off at about 130° C. This stream was isomerised in the gas phase as described in example I of EP-A-192298; by using a 3x larger catalyst bed it was ensured that the degree of conversion of the cyclohexene oxide remained above 95%. The resulting isomerisation mixture contained cyclohexanone and cyclohexanol in a ratio of 4:1.

EXAMPLE II

In the same way as in example I a 40% solution of cyclohexene in cyclohexane was epoxidized with cyclohexylhydroperoxide (40%) using 0.2 mol. % molybdenum-bis-acetylacetonate as a homogeneous catalyst (20% excess cyclohexylhydroperoxide). The results were more or less the same as those obtained in example I.

We claim:

1. Process for the production of cycloalkanone and optionally cycloalkanol comprising:

causing a mixture containing cycloalkylhydroperoxide to react with a cycloalkene under the influence of a catalyst, wherein the reaction is conducted with a short measure of cycloalkene relative to the cycloalkylhydroperoxide, under such conditions that virtually all of the cycloalkene reacts to cycloalkene oxide and optionally cycloalkanol and/or cycloalkanone, after which, subjecting the mixture, optionally after decomposition of cycloalkylhydroperoxide and distillation of cycloalkane, to a first separation, in which at least cycloalkene oxide is separated therefrom, isomerizing the cycloalkene oxide in the separated mixture to substantially cycloalkanone, and recovering at least the cycloalkanone.

2. Process according to claim 1, wherein the cycloalkylhydroperoxide has 5-12 carbon atoms.

3. Process according to claim 1 wherein the cycloalkene has 5-12 carbon atoms.

4. Process according to claim 1, wherein the cycloalkylhydroperoxide has the same number of carbon atoms as the cycloalkene.

5. Process according to claim 4, wherein the cycloalkylhydroperoxide is cyclohexylhydroperoxide and the cycloalkene is cyclohexene.

6. Process according to claim 1, wherein, optionally after purification, the mixture obtained after the isomerization is added to the first separation step with the provisos that the first separation step is a distillative separation having a bottom stream and the addition is to the bottom stream, or that mixture is used in a later step in the recovery of cycloalkanone and/or cycloalkanol.

7. Process according to claim 6, for the preparation of cycloalkanone, wherein cycloalkanone is recovered in a further distillation step, after which cycloalkanol is separated from the residue and is converted into cycloalkanone, which is recirculated and is recovered in the distillative step.

8. Process according to claim 1, wherein the mixture containing cycloalkylhydroperoxide contains 5-90 wt. % cycloalkylhydroperoxide.

9. Process according to claim 1, wherein a metal complex is used as a catalyst and the metal is selected from the group consisting of molybdenum, tungsten, titanium and vanadium.

10. Process according to claim 1, wherein cycloalkylhydroperoxide is used in an excess of 5-100 mol. %, relative to the cycloalkene.

11. Process according to claim 1, wherein the isomerization of cycloalkene oxide takes place in the gas phase.

12. Process according to claim 1, wherein the isomerization takes place under the influence of a precious metal catalyst.

* * * * *

UNITED STATES PATENT AND TRADEMARK OFFICE
CERTIFICATE OF CORRECTION

PATENT NO.    :    5,334,768

DATED         :    AUGUST 2, 1994

INVENTOR(S)   :    van HINSBERG et al

It is certified that error appears in the above-identified patent and that said Letters Patent is hereby corrected as shown below:

On the title page, item:

change:

"[30] FOREIGN APPLICATION PRIORITY DATA

March 2, 1992   [NL] . . ."

to

--[30] FOREIGN APPLICATION PRIORITY DATA

February 3, 1992   [NL] . . . --

Signed and Sealed this

Twenty-seventh Day of February, 1996

Attest:

BRUCE LEHMAN

*Attesting Officer*    *Commissioner of Patents and Trademarks*